United States Patent
Osbakken et al.

(10) Patent No.: US 8,337,814 B2
(45) Date of Patent: *Dec. 25, 2012

(54) TREATMENT OF ACTIVE INFECTIONS, SINUSITIS, RHINITIS, AND RELATED NEUROLOGICAL DISORDERS AND RELATED COMPOSITIONS

(75) Inventors: Robert Scott Osbakken, Camarillo, CA (US); Russell N. Reitz, Camarillo, CA (US); John C. Tarrant, Camarillo, CA (US)

(73) Assignee: Topical Sinus Therapeutics, Inc., Camarillo, CA (US)

(*) Notice: Subject to any disclaimer, the term of this patent is extended or adjusted under 35 U.S.C. 154(b) by 999 days.

This patent is subject to a terminal disclaimer.

(21) Appl. No.: 12/097,230

(22) PCT Filed: Dec. 15, 2006

(86) PCT No.: PCT/US2006/062170
§ 371 (c)(1), (2), (4) Date: Nov. 13, 2008

(87) PCT Pub. No.: WO2007/070875
PCT Pub. Date: Jun. 21, 2007

(65) Prior Publication Data
US 2009/0142277 A1    Jun. 4, 2009

(51) Int. Cl.
*A61K 9/12* (2006.01)
*A61M 11/00* (2006.01)
(52) U.S. Cl. .......... 424/43; 128/200.14; 128/200.23
(58) Field of Classification Search ............ 424/43; 128/200.14, 200.23, 204.23
See application file for complete search history.

(56) References Cited

U.S. PATENT DOCUMENTS

| | | | | |
|---|---|---|---|---|
| 5,152,456 A * | 10/1992 | Ross et al. | ............. | 239/102.2 |
| 5,508,269 A * | 4/1996 | Smith et al. | ............. | 514/38 |
| 6,098,620 A * | 8/2000 | Lloyd et al. | ............. | 128/204.23 |
| 6,576,224 B1 * | 6/2003 | Osbakken et al. | ............. | 424/45 |
| 7,128,897 B2 * | 10/2006 | Osbakken et al. | ............. | 424/45 |
| 2002/0061281 A1 * | 5/2002 | Osbakken et al. | ............. | 424/43 |
| 2004/0209852 A1 * | 10/2004 | Chaudry | ............. | 514/171 |
| 2005/0004020 A1 * | 1/2005 | Yu et al. | ............. | 514/12 |
| 2005/0009923 A1 | 1/2005 | Banerjee | | |
| 2007/0202051 A1 * | 8/2007 | Schuschnig | ............. | 424/45 |

FOREIGN PATENT DOCUMENTS

EP    1527772    5/2005
WO   WO2004052333    6/2004

OTHER PUBLICATIONS

Giannoni et al. "Intracranial Complications of Sinusitis," The Laryngoscope, Jul. 1997, 107, pp. 863-867.*
Sinusitis from the online Merck Manual Home Edition accessed on Sep. 14, 2011 at www.merckmanuals.com/home/print/ear_nose_and_throat_disorders/nose_sinus_and_taste_disorders/sinusitis.html.*
"Rhinitis" from the online Merck Manual Home Edition accessed on Sep. 14, 2011 at www.merckmanuals.com/home/print/ear_nose_and_throat_disorders/nose_sinus_and_taste_disorders/rhinitis.html.*
1999 Drug Information Handbook, Lexi-Comp, Inc.: Hudson, OH, pp. 385-386 (etanercept entry).*

* cited by examiner

*Primary Examiner* — James H. Alstrum-Acevedo
(74) *Attorney, Agent, or Firm* — Sheppard Mullin Richter & Hampton LLP

(57) ABSTRACT

The present invention is directed to the treatment of infections and the associated symptoms of sinusitis, rhinitis and related neurological disorders of the cranial cavity and facial tissue. More specifically, the present invention is directed to aerosols that are used to treat infections and the associated symptoms of sinusitis, rhinitis and related neurological disorders of the cranial cavity and facial tissue, compositions from which the aerosols are generated and methods of generating the aerosols. In an aerosol aspect of the present invention, an aerosol for delivery to the sinus cavity of a patient is provided. The aerosol includes at least: a) one or more compounds selected from antibiotics, antifungals, leukotriene antagonists, anti-TNF compounds, antihistamines, steroidal antiinflammatories, mucolytics, estrogen, progesterone and related hormones; and, b) water The compounds are present in the water at a concentration ranging from 0.01 mg/kg to 1000 mg/kg, and the aerosol does not contain a surfactant.

28 Claims, No Drawings

# TREATMENT OF ACTIVE INFECTIONS, SINUSITIS, RHINITIS, AND RELATED NEUROLOGICAL DISORDERS AND RELATED COMPOSITIONS

FIELD OF THE INVENTION

The present invention is directed to the treatment of sinusitis, rhinitis and related neurological disorders of the cranial cavity and facial tissue. More specifically, the present invention is directed to aerosols that are used to treat sinusitis, rhinitis and related neurological disorders of the cranial cavity and facial tissue, compositions from which the aerosols are generated and methods of generating the aerosols.

BACKGROUND OF THE INVENTION

U.S. Pat. No. 7,128,897 discusses pharmaceutical compositions formulated for aerosol administration to the nasal sinuses. The compositions contain one agent for treatment of sinusitis and a surfactant; they further have a surface tension between 10 dynes/cm and 70 dynes/cm.

The compositions are aerosolized using a nebulizer. such as a the RESPIRONICS®Sidestream jet nebulizer and the Pari LC jet nebulizer. According to the patent, the resulting aerosols have a mass median aerodynamic diameter between 0.5 µm and 5.0 µm. A stated objective is to produce aerosols where less than 20% of the particles are over 5.0 µm in diameter. There is no indication within the four corners of the document, however, indicating that such a distribution was achieved.

In view of the disclosure presented in U.S. Pat. No. 7,128,897, there remains a need for aerosolization methods and related compositions that may be used to treat sinusitis, rhinitis and related neurological disorders of the cranial cavity and facial tissue.

SUMMARY OF THE INVENTION

The present invention is directed to the treatment of sinusitis, rhinitis and related neurological disorders of the cranial cavity and facial tissue. More specifically, the present invention is directed to aerosols that are used to treat sinusitis, rhinitis and related neurological disorders of the cranial cavity and facial tissue, compositions from which the aerosols are generated and methods of generating the aerosols.

In an aerosol aspect of the present invention, an aerosol for delivery to the sinus cavity of a patient is provided. The aerosol includes at least: a) one or more compounds selected from antibiotics, antifungals, leukotriene antagonists, anti-TNF compounds, antihistamines, anti-inflammatories, mucolytics; estrogen, progesterone and their related hormones; and, b) solvent. The compounds are present in the solvent at a concentration ranging from 0.01 mg/ml to 1000 mg/ml, and the liquid does not require a surfactant or other additive to aerosolize optimally.

In another aerosol aspect of the present invention, an aerosol for delivery to the sinus cavity of a patient is provided. The aerosol includes at least: a) one or more compounds selected from antibiotics, anti-fungals, leukotriene antagonists, anti-TNF compounds, antihistamines, anti-inflammatories, mucolytics; estrogen, progesterone and their related hormones; and, b) a solvent. The compounds are present in the solvent at a concentration ranging from 0.01 mg/ml to 1000 mg/ml, and the aerosol does not require a surfactant or other additive to aerosolize optimally. The aerosol is made using a method having at least the following steps: a) placing an aqueous composition comprising one or more compounds selected from a group consisting of antibiotics, antifungals, leukotriene antagonists, anti-TNF compounds, antihistamines, steroidal antiinflammatories, mucolytics; estrogen, progesterone and their related hormones into a medication reservoir of a nasal filtration aerosolizing device; and, b) forcing the composition through pores of the filter.

In a method of treatment aspect, methods of treating sinusitis, rhinitis and related neurological disorders of the cranial cavity and facial tissue are provided. The methods involve administration of the aerosols listed previously to a patient.

DETAILED DESCRIPTION OF THE INVENTION

The present invention is directed to the treatment of sinusitis, rhinitis and related neurological disorders of the cranial cavity and facial tissue. More specifically, the present invention is directed to aerosols that are used to treat sinusitis, rhinitis and related neurological disorders of the cranial cavity and facial tissue, compositions from which the aerosols are generated and methods of generating the aerosols.

Compositions used to generate the aerosols of the present invention typically include one or more compounds selected from the following classes of compounds: antibiotics, antifungals, leukotriene antagonists, anti-TNF compounds, antihistamines, anti-inflammatories, mucolytics; estrogen, progesterone and their related hormones. The compositions further typically include a solvent, such as water The concentration of compounds in the solvent usually ranges from 0.01 mg/ml to 1000 mg/ml, depending on the appropriate dose of the compound. The compositions do not not require a surfactant or other additive to aerosolize optimally Furthermore, the compositions may have an osmolality either within or outside of the range of 200 mOsm/kg to 880 mOsm/kg.

Nonlimiting examples of antibiotics include the following compound classes: cephalosporins($1^{st}$-$4^{th}$ generation), penicillins, aminoglycosides, quinolones, tetracyclines, and macrolides. Nonlimiting examples of antivirals are oseltamivir, acyclovir, and rimantadine. Nonlimiting examples of antifungals are Amphotericin B, fluconazole, Itraconazole, and all forms of liposomal amphotericin. Nonlimiting examples of leukotriene antagonists are montelukast, and zafirlukast. Nonlimiting examples of anti-TNF compounds are infliximab, etanercept, and adalimumab. A nonlimiting examples of an antihistamine is azelastin. Nonlimiting examples of steroidal anti-inflammatories are budesonide, betamethasone, and mometasone. Nonlimiting examples of mucolytics are acetylcysteine, dornase alpha and saline solution. Nonlimiting examples of estrogen, progesterone and their compounds, natural or synthetic, include estradiol, estriol and estrone; and progesterone manufactured from soy or yam.

Aerosols are typically generated from compositions of the present invention using a nasal filtration aerosoling device including the following: 1) A filter with consistent 1 µm to 6 µm holes or pores. The pores are spaced relatively evenly across the filter at 15 to 150 µm between centers. The filter turns liquid medications forced through it into an aerosol. It may or may not be attached to a motor, which would vibrate the filter to increase flow through the filter. 2) A medication reservoir holding from 0.5 mL to 10 mL of the composition of the present invention. In an optimal configuration, the reservoir is sealed and pressurized to enhance liquid flow through the filter after filling. 3) A small pump or mechanical piston to pressurize the medication reservoir to between 30 and 300 psi. 4) An electronic device that creates A/C current at between 25 k and 30 k hertz to connect to electromagnets and that would vibrate the filter. 5) An aerosol reservoir to hold the aerosol after it has been created. The reservoir is typically at least 20 mL and not more than 200 mL in volume. 6) A nosepiece that has two openings with diameters from 0.25 inches to 0.4 inches and with the centers of the openings spaced between 0.55 inches and 0.7 inches apart Where a nasal filtration aerosolizing device is used, it's basic operation is as follows: A composition of the present invention (e.g., 1 mL to 6 mL) is poured into the medication reservoir or a unit dose container of the composition is attached to the medication reservoir. A small battery operated pump generates air pressure above the composition. A mechanical valve is turned on to allow the pressurized composition to come in contact with the filter. The same mechanism that opens the valve starts the filter vibrating. Liquid is forced through the filter and the resulting aerosol fills the aerosol reservoir. A patient holds the device with the holes in the nosepiece between ¼ inch and 1 inch below his nostrils. A one-way air valve at the opposite end of the aerosol reservoir from the inhalation holes allows air to come into the aerosol reservoir as the patient inhales. The resulitng aerosol enters the patient's nasal cavities and a percentage disperses into the sinuses.

The aerosols of the present invention are characterized by their controllable size range. The mass median aerodynamic diameter (MMAD) of the aerosols ranges from 1.0 μm to 5.5 μm. It typically ranges from 2.0 μm to 5.0 μm. In certain cases, the MMAD ranges from 2.5 μm to 3.5 μm or 2.7 μm to 3.3 μm.

Moreover, 85% of the particles usually have an aerodynamic diameter ranging from 1.0 μm to 4.5 μm. Typically, 85% of particles have an aerodynamic diameter ranging from 1.5 μm to 3.5 μm.

Aerosols, as do the compositions from which the aerosols arise, typically include one or more compounds selected from the following classes of compounds: antibiotics, antifungals, leukotriene antagonists, anti-TNF compounds, antihistamines, steroidal antiinflammatories, mucolytics; estrogen, progesterone and their related hormones. The following are nonlimiting examples where more than one compound is included: one antibiotic and one antifungal; one antibiotic and one leukotriene antagonist; one antibiotic and one anti-TNF compound; one antibiotic and one antihistamine; one antibiotic and one steroidal anti-inflammatory; one antibiotic and one mucolytic. The aerosols do not contain a surfactant.

Compounds contained in the aerosols are not substantially degraded by the aerosolization process. For instance, the compounds are typically at least 97% pure, are oftentimes at least 98% pure and are at least 99% pure is some cases.

The time of a single administration of an aerosol of the present invention typically varies from 1 minute to 8 minutes in length, depending on the composition used in the aerosolization device. Oftentimes, treatment involves from one to three aerosol administrations per day and, in most cases, the duration of treatment is 7 to 30 days, and often ongoing for prophylaxis. Aerosols of the present invention are used to treat a variety of different infections and resulting symptoms. Aerosols including one or more antibiotics are used to treat sinus infections; aerosols including one or more antinflammatories are used to reduce the incidence of sinus infections, polyps, allergic symptoms and headaches; aerosols including one or more antifungals are used to treat fungal infections, which are thought to cause an increased incidence of sinus infections, polyps, allergic rhinitis and headaches; aerosols including one or more anti-virals are used to alleviate symptoms of various strains of flu and colds, which often lead to bacterial sinus infections; aerosols containing one or more mucolytics are used to reduce the incidence of sinus infections by liquefying crusted mucous and promoting mucous production in patients with dry sinus cavities; and aerosols containing estrogen, progesterone or their related hormones are used to thicken epithelial tissue within the sinuses preventing infection.

The invention claimed is:

1. A method of delivering a medication aerosol for treating sinusitis or rhinitis, and related neurological disorders of the cranial cavity and facial tissue, wherein the method comprises creating the medication aerosol by passing a liquid composition through a filter, wherein:
   the filter comprises pores;
   the medication aerosol and the liquid composition do not contain a surfactant: and
   the liquid composition comprises one or more compounds selected from the group consisting of antifungals, leukotriene antagonists, anti-TNF compounds, antihistamines, mucolytics, estrogen and progesterone.

2. The method according to claim 1, wherein the filter pores range in size from 1 μm to 6 μm.

3. The method according to claim 2, wherein the filter pores are placed such that the distance between filter pore centers ranges from 15 μm to 150 μm.

4. The method according to claim 3, wherein the liquid composition comprises an antibiotic, and wherein the antibiotic is selected from the group of antibiotic classes consisting of: cephalosporins, penicillins, aminoglycocides, quinolones, tetracyclines and macrolides.

5. The method according to claim 3, wherein the liquid composition comprises an antiviral, and wherein the antiviral is selected from the group consisting of oseltamivir, acyclovir and rimantadine.

6. The method according to claim 3, wherein the liquid composition comprises an antifungal, and wherein the antifungal is selected from the group consisting of amphotericin B, fluconazole, itraconazole and liposomal amphotericin.

7. The method according to claim 3, wherein the liquid composition comprises a leukotriene antagonist, and wherein the leukotriene antagonist is selected from the group consisting of montelukast and zafirlukast.

8. The method according to claim 3, wherein the liquid composition comprises an antihistamine, and wherein the antihistamine is azelastin.

9. The method according to claim 3, wherein the liquid composition comprises a steroidal anti-inflammatory and wherein the anti-inflammatory is selected from the group consisting of budesonide, betamethasone and mometasone.

10. The method according to claim 3, wherein the liquid composition comprises a mucolytic, and wherein the mucolytic is selected from the group consisting of acetylcysteine and dornase alpha.

11. The method according to claim 1, wherein the liquid composition is stored in a reservoir being sealed and pressurized.

12. The method according to claim 11, wherein the reservoir is pressurized between 30 psi and 300 psi.

13. The method according to claim 11, wherein the reservoir is pressurized by a pump or by a mechanical piston.

14. The method according to claim 1, wherein the liquid composition comprises one or more compounds selected from the group consisting of anti-TNF compounds, estrogen, and progesterone.

15. A medication aerosol for delivery to the sinus cavity of a patient, wherein the aerosol comprises:
   (a) one or more compounds selected from antifungals, leukotriene antagonists, anti-TNF compounds, antihistamines, mucolytics, estrogen and progesterone; and
   (b) water; wherein:
   the compounds are present in the water at a concentration ranging from 0.01 mg/ml to 1000 mg/ml;

the medication aerosol is made using a method comprising creating the medication aerosol by passing a liquid composition through a filter, and wherein the filter comprises pores, thereby forming the aerosol; and the medication aerosol and the liquid composition do not contain a surfactant.

16. The aerosol according to claim 15, wherein the filter pores range in size from 1μm to 6μm.

17. The aerosol according to claim 16, wherein the filter pores are placed such that the distance between filter pore centers ranges from 15 μm to 150 μm.

18. The aerosol according to claim 17, wherein the aerosol comprises an antiviral, and wherein the antiviral is selected from the group consisting of oseltamivir, acyclovir and rimantadine.

19. The aerosol according to claim 17, wherein the aerosol comprises an antifungal, and wherein the antifungal is selected from the group consisting of amphotericin B, fluconazole, itraconazole and liposomal amphotericin.

20. The aerosol according to claim 17, wherein the aerosol comprises a leukotriene antagonist, and wherein the leukotriene antagonist is selected from the group consisting of montelukast and zafirlukast.

21. The aerosol according to claim 17, wherein the aerosol comprises an anti-TNF compound, and wherein the anti-TNF compound is selected from the group consisting of infliximab, etanercept, adalimumab.

22. The aerosol according to claim 17, wherein the aerosol comprises an antihistamine, and wherein the antihistamine is azelastin.

23. The aerosol according to claim 17, wherein the aerosol comprises a steroidal antiinflammatory, and wherein the antiinflammatory is selected from the group consisting of budesonide, betamethasone and mometasone.

24. The aerosol according to claim 17, wherein the aerosol comprises a mucolytic, and wherein the mucolytic is selected from the group consisting of acetylcysteine and dornase alpha.

25. The aerosol according to claim 15, wherein the liquid composition is stored in a reservoir being sealed and pressurized.

26. The aerosol according to claim 25, wherein the reservoir is pressurized between 30 psi and 300 psi.

27. The aerosol according to claim 25, wherein the reservoir is pressurized by a pump or by a mechanical piston.

28. The aerosol according to claim 15, wherein the liquid composition comprises one or more compounds selected from the group consisting of anti-TNF compounds, estrogen, and progesterone.

* * * * *